United States Patent
Maeda et al.

(10) Patent No.: US 7,465,049 B2
(45) Date of Patent: Dec. 16, 2008

(54) PORTABLE OPHTHALMIC APPARATUS AND OPHTHALMIC SYSTEM

(75) Inventors: Naoyuki Maeda, Osaka (JP); Yoko Hirohara, Tokyo (JP); Toshifumi Mihashi, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 332 days.

(21) Appl. No.: 10/525,540

(22) PCT Filed: Aug. 13, 2003

(86) PCT No.: PCT/JP03/10276

§ 371 (c)(1), (2), (4) Date: Feb. 24, 2005

(87) PCT Pub. No.: WO2004/017825

PCT Pub. Date: Mar. 4, 2004

(65) Prior Publication Data

US 2005/0270484 A1     Dec. 8, 2005

(30) Foreign Application Priority Data

Aug. 26, 2002   (JP) .............................. 2002-244811

(51) Int. Cl.
A61B 3/10      (2006.01)
(52) U.S. Cl. ....................................................... 351/205
(58) Field of Classification Search ................. 351/205, 351/206, 208, 210, 212, 214, 221
See application file for complete search history.

(56) References Cited

U.S. PATENT DOCUMENTS 5,150,146 A    9/1992   Ueda et al.
6,283,596 B1   9/2001   Yashimura et al.

FOREIGN PATENT DOCUMENTS

| EP | 0947159 A1 | 10/1999 |
| WO | WO 97/36537 | 10/1997 |
| WO | WO 97/36537 A1 | 10/1997 |
| WO | WO 01/20561 | 3/2001 |

OTHER PUBLICATIONS

Shi Mingguang, "Development of Reflective Keratoscope," Journal of Wenzhou Medical College, 1991, pp. 88-90, vol. 2.

Gao Yaping, "Common Test Instrument for the Optometry and Selection of Contact Lenses: Slit Lamp Microscope and Instrument of Cornea Curvature," China Glasses Science-Technology Magazine, 1998, pp. 24-28, vol. 3.

*Primary Examiner*—Hung X. Dang
*Assistant Examiner*—Tuyen Q Tra
(74) *Attorney, Agent, or Firm*—Chapman and Cutler LLP

(57) ABSTRACT

A portable ophthalmic apparatus (1) according to the present invention comprises a supporting part (7) to which a cellular phone (2) having a photographing camera (5) is mounted detachably and a main body (6) which is provided with the supporting part (7) integrally and has an illumination optical system (13) projecting an illumination beam toward photographing objective eyes (E) along an illumination optical axis (O2) intersected at a predetermined angle with a photographing optical axis (O1).

17 Claims, 13 Drawing Sheets

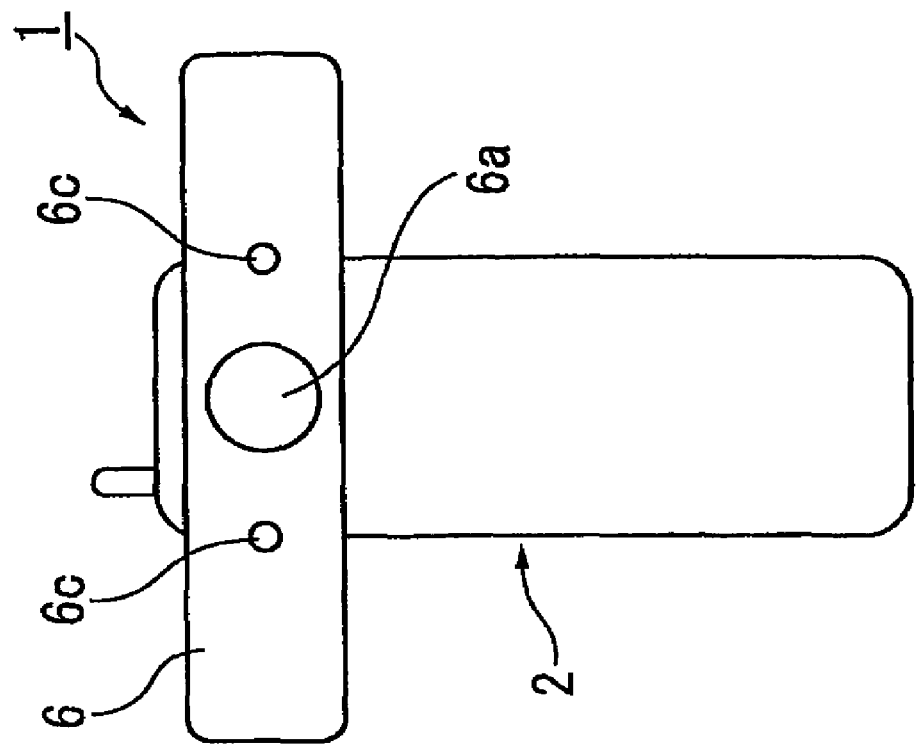
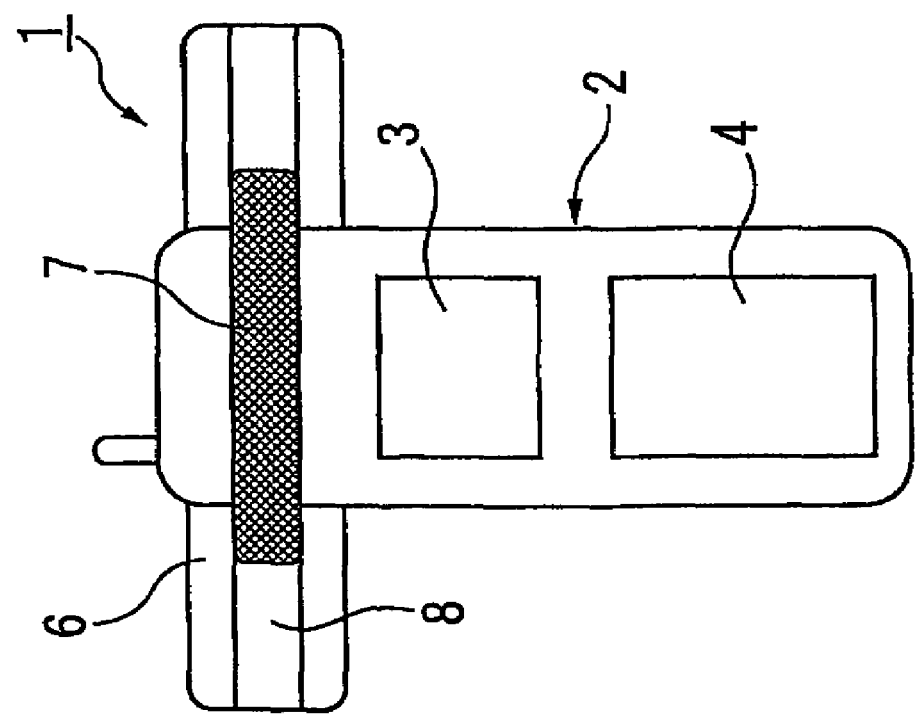

F I G. 5
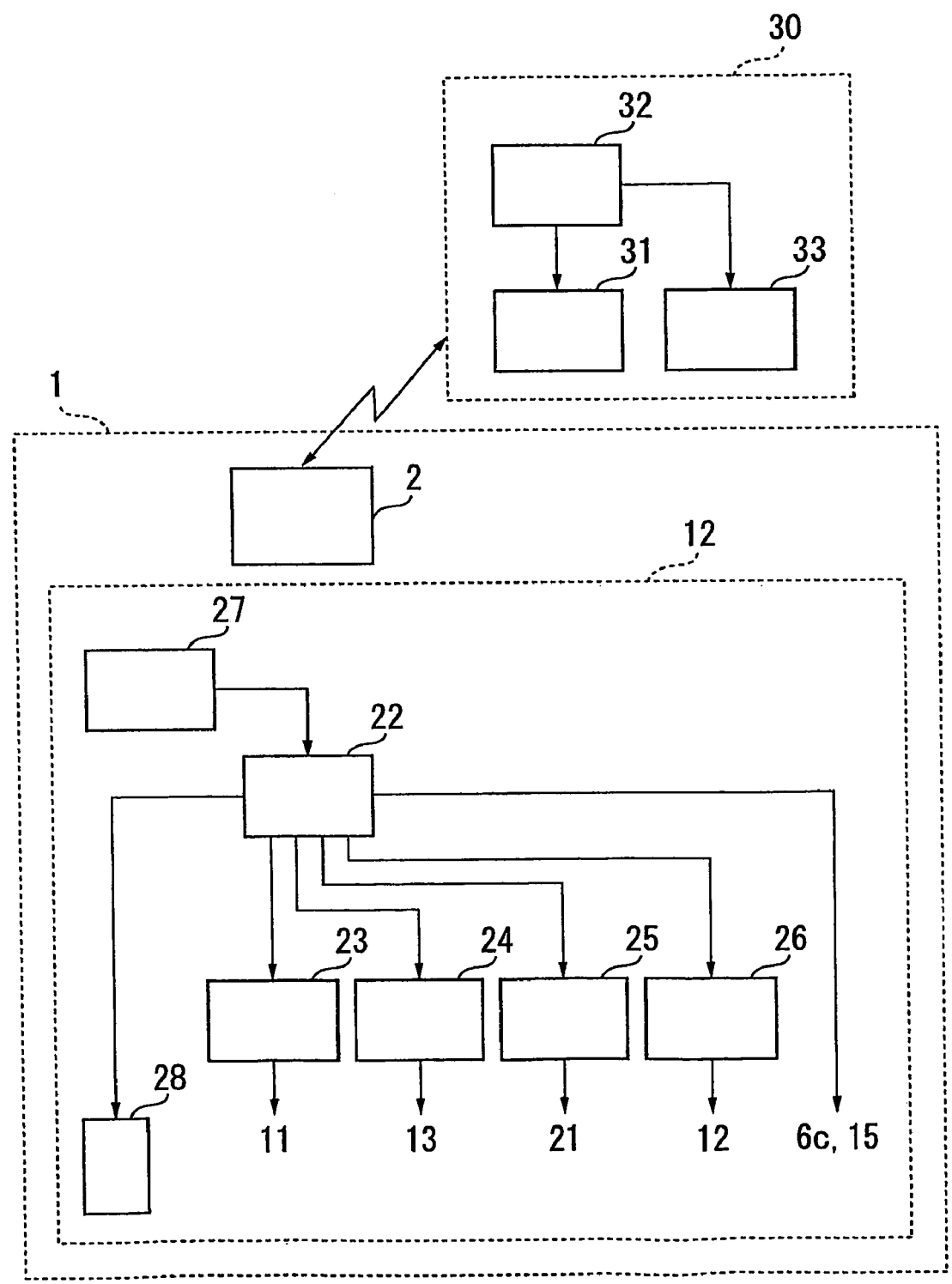

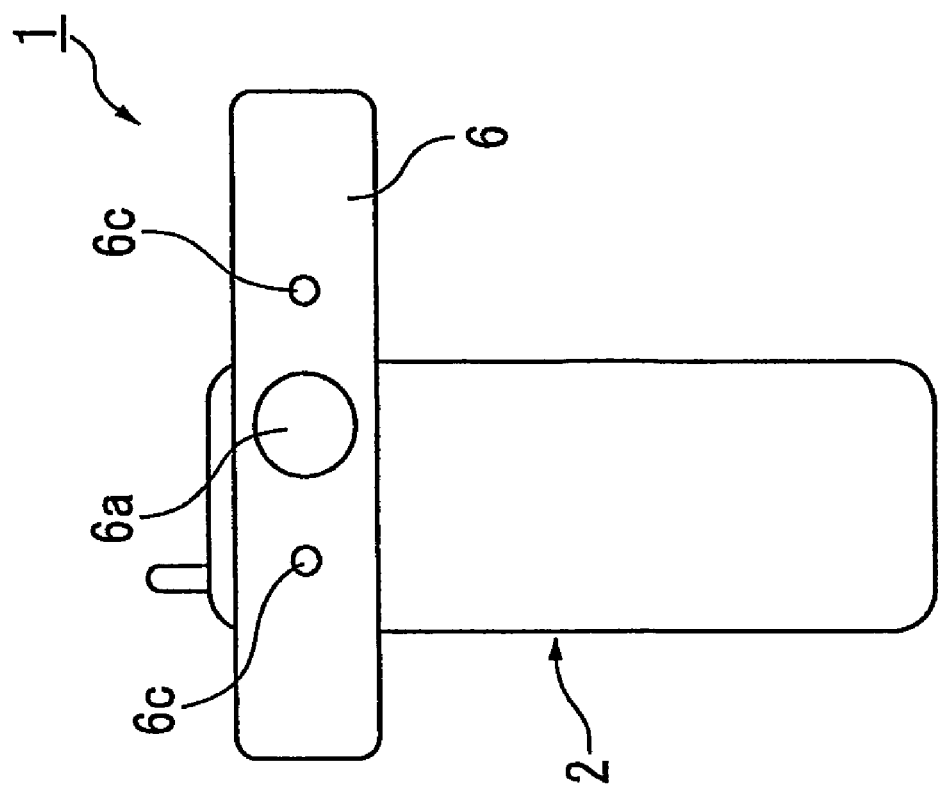
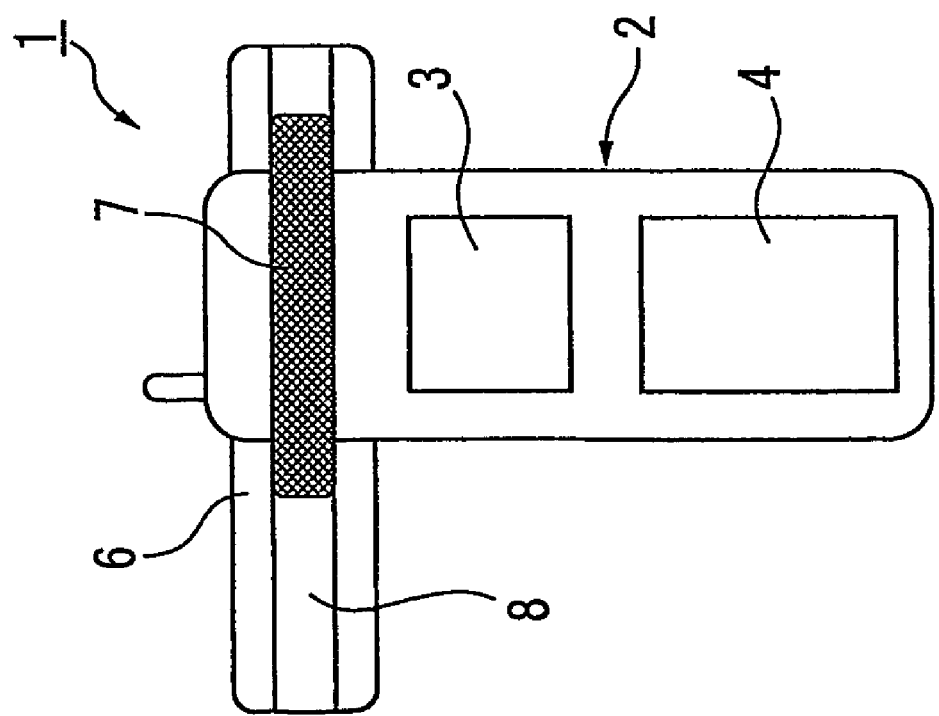

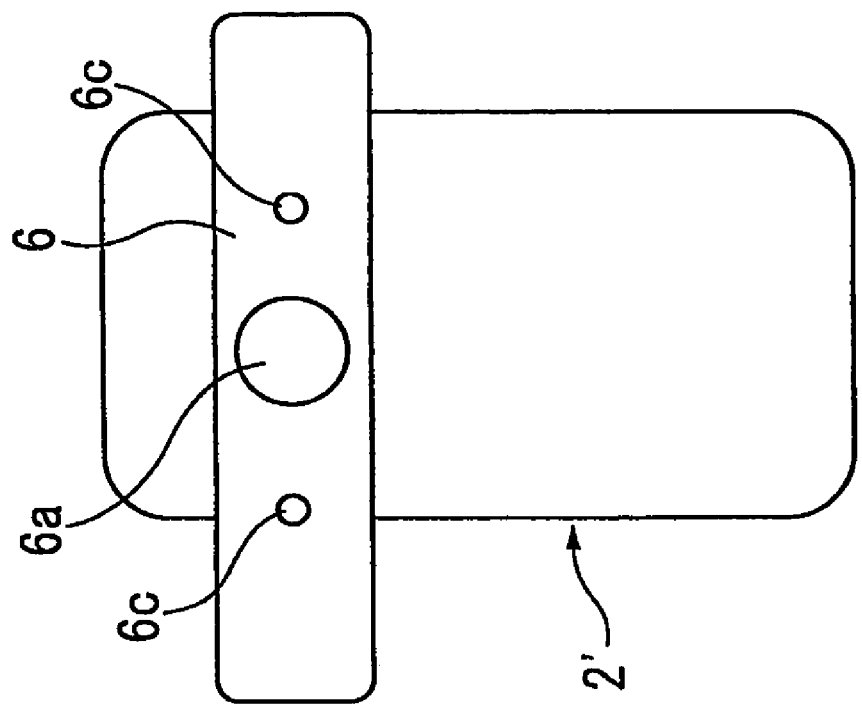
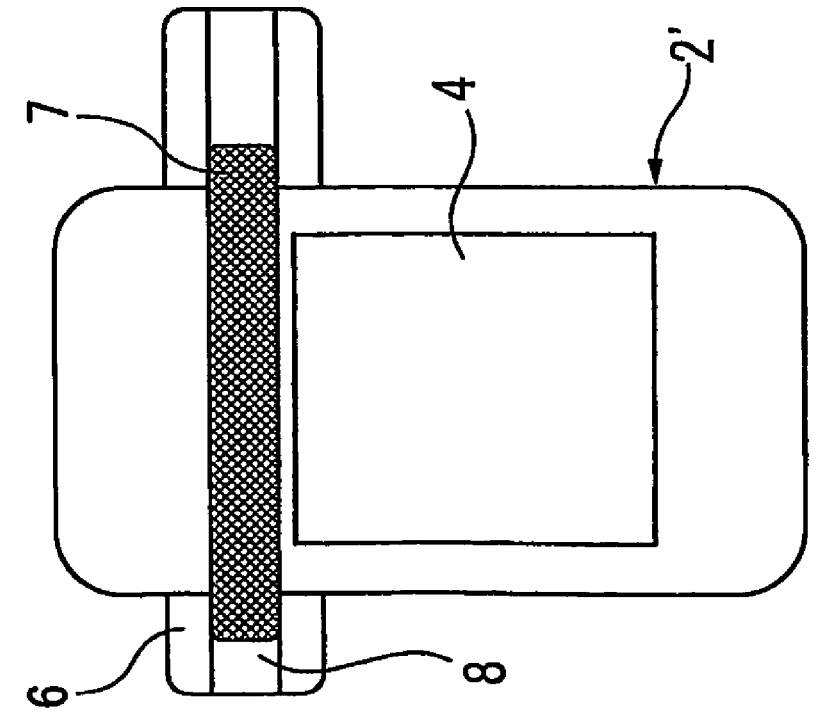

PORTABLE OPHTHALMIC APPARATUS AND OPHTHALMIC SYSTEM

TECHNICAL FIELD

The present invention relates to a portable ophthalmic apparatus capable of obtaining image data of photographing objective eyes by use of prevailing portable devices having a photographing function such as a cellular phone, a personal digital assistance (PDA), and a digital camera, and to an ophthalmic system capable of processing image data by utilizing a telecommunication function of the portable ophthalmic apparatus.

BACKGROUND ART

Conventionally, as ophthalmic apparatuses, there are known a slit lump apparatus, a fundus camera, a reflecting power measuring apparatus, a corneal endothelium photographing apparatus, and so on. These ophthalmic apparatuses are mainly equipped in medical offices.

For instance, the slit lump apparatus radiates slit illuminating light beam toward photographing objective eyes and then observes and photographs the photographing objective eyes illuminated by the slit illuminating light beam.

In the conventional slit lump apparatus, a patient is sit in front the slit lump apparatus. Then, a photograph of the photographing objective eyes is taken by carrying out an alignment adjustment which makes up-down and right-left alignments of a photographing optical axis of the apparatus relative to the eyes (alignments in a direction orthogonal to the optical axis) and an operational distance adjustment (alignment in the direction of the optical axis) which is an alignment of the slit lump apparatus relative to the photographing objective eyes, and carrying out a focusing adjustment if needed.

The observation of the patient's eyes is really effective for ophthalmic diagnostic treatment.

However, the conventional ophthalmic apparatuses are not available mainly except for medical offices. Therefore, there are inconveniences to obtain graphic data of the patient's eyes at outside of the medical offices when the condition of the patient's eye promptly needs to be recorded or when the doctor cannot diagnose the patient directly because a doctor and a patient are separated far away.

It is an object of the present invention to provide a portable ophthalmic apparatus which is capable of obtaining graphic data of objective eye with a portable photograph function such as prevailing portable cellular phone containing photo function, a personal digital assistance (PDA), a digital camera, and so on, also, and to provide an ophthalmic system which processes the graphic data by use of telecommunication function of the portable ophthalmic apparatus.

DISCLOSURE OF INVENTION

A portable ophthalmic apparatus according to the present invention is characterized in that it has a supporting part which attaches detachably a portable device having a photographing camera part to a photographing optical axis, and a main body which is capable of mounting integrally the supporting part and has an illustration optical system that radiates an illumination beam toward the photographing objective eyes along an illumination optical axis intersected at the predetermined angle with the photographing optical axis.

It is preferable that an illumination condition of the illumination optical system can be changed.

It is more preferable that the portable device is a personal digital assistance that has a part of telecommunication function.

The illumination condition may be determined by an angle that is formed by the photographing optical axis and the illumination optical axis, shape of or amount of illumination optical beam. It is much more preferable that the main body has a photographing assistant optical system and the photographical condition thereof can be changed in accordance with variation of illumination conditions.

It is convenient that the photographical assistant optical system has a zoom lens or an auxiliary lens, and the auxiliary lens can be set and level of zoom of the zoom lens can be changed in accordance with a photographical condition.

It is more convenient that the main body is constructed so that optical units are different in structure can be set to replace. If the illumination optical system has a slit aperture stop, by projecting illumination beam of slit toward the object eye, it is possible to photograph cross section shapes of a cornea and a crystal line lens. It is possible to change a part of eye ground to be photographed if the main body has a photographing assistant optical system for photographing the eye ground of the object eye and the illumination optical system is able to change the angle of the photographing optical axis.

By setting up a concentric placido-disc illumination optical system in the main body, it is possible to ring-illustrate the cornea of object eye so that the shape of cornea can be observed. If the supporting part has a pair of legs adapted to approach and separate or extend and contract with respect to each other, a various type of portable devices may be used for the portable ophthalmic apparatus.

It is more preferable that the supporting part is slidable relative to the main part. It is convenient that the data are processed at the end destination if a command function is provided, which processes the graphic data of the object eye at the destination even though the data analyzed function is not equipped in the portable device. It is more convenient if literal and symbol data as well as graphic data are transmittable.

BRIEF DESCRIPTION OF DRAWINGS

FIG. 1 is a schematic diagram showing an example of a portable ophthalmic apparatus according to the present invention, in which (a) is a view of the portable ophthalmic apparatus equipped with a cellular phone, as viewed from a front of the cellular phone, and (b) is a view of the portable ophthalmic apparatus as viewed from a back of the cellular phone.

FIG. 5 is an explanatory view of a control circuit of the portable ophthalmic apparatus according to the present invention.

FIG. 8 is an explanatory view of the portable ophthalmic apparatus to which the cellular phone shown in FIG. 7 is attached, in which (a) is a front view of the cellular phone, and (b) is a back view thereof.

FIG. 9 is an explanatory view of the portable ophthalmic apparatus to which a PDA is attached as the portable device, in which (a) is a front view of the PDA, and (b) is a back view thereof.

BEST MODE FOR CARRYING OUT THE INVENTION (Mode 1 for Carrying Out the Invention)

Figure 2A:
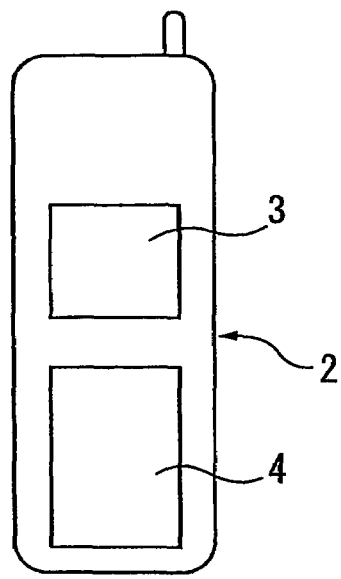
FIG. 2 is a schematic diagram showing the cellular phone which can be attached to the portable ophthalmic apparatus, in which (a) is a view as viewed from the front thereof and (b) is a view as viewed from the back thereof.
Figure 2B:
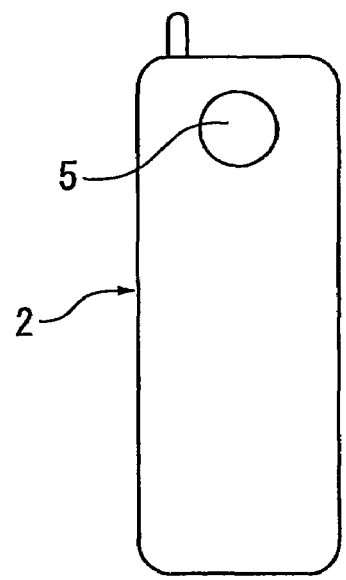

FIG. 1 illustrates a state that a cellular phone 2 as a portable device is attached to a portable ophthalmic apparatus 1, which relate to the invention. As shown in FIG. 2(a), the cellular phone 2 has on its front surface a monitor screen 3 and a 10-key numeric keypad 3. A back surface of the cellular phone is provided at its upper part and central part in a direction of width with a photographing lens 5 consisting a part of a photographical camera, as shown in FIG. 2(b).

The portable ophthalmic apparatus 1 is generally composed of a main body 6 and a supporting part 7. The supporting part 7 is provided integrally with the main body 6. The main body 6 has a dovetail groove 8 in a surface of the side to which the supporting part is attached.

Figure 3:
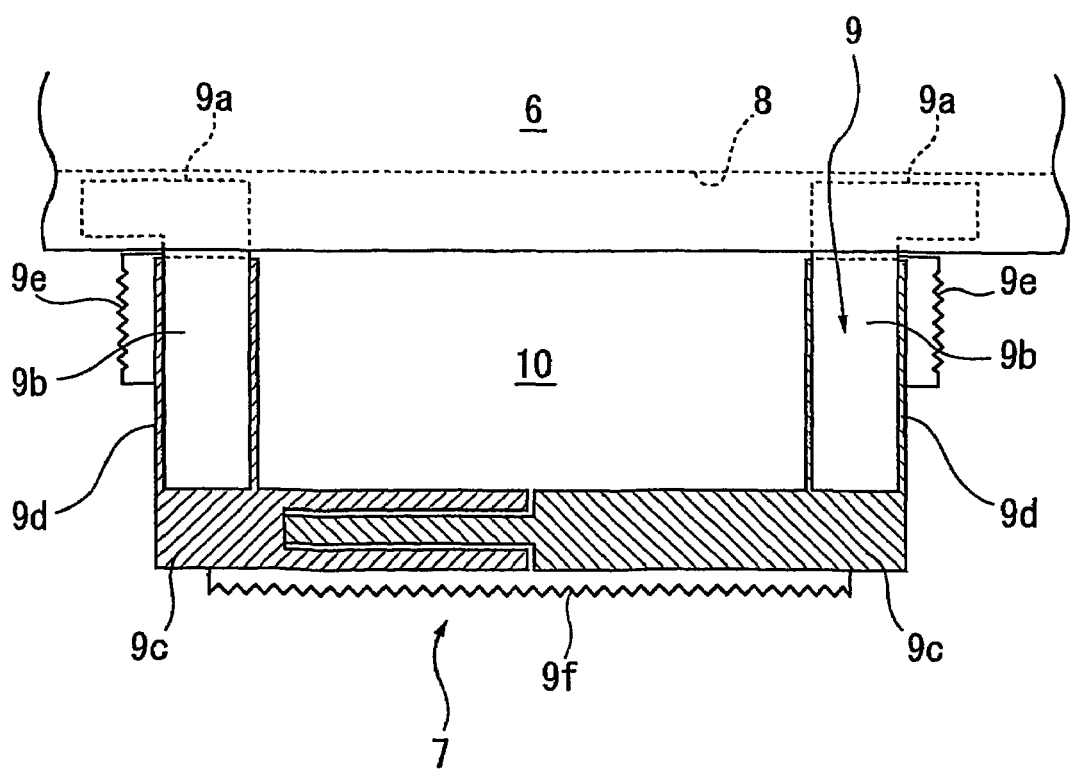
FIG. 3 is a fragmentary sectional view for explaining a detailed structure of a supporting part shown in FIG. 1(b).

As shown in detail in FIG. 3 of an enlarged view, the supporting part 7 has a pair of legs 9 and 9. The legs have engaging parts 9a and 9a which are adapted to engage in the dovetail groove 8 and support pillars 9b and 9b. The legs 9 and 9 are slidable longitudinally of the dovetail groove 8.

The support pillars 9b are provided with fitting tubes 9d and 9d which are extendable longitudinally of the pillars. The fitting tubes 9d and 9d are biased such that they get close to the main body 6 by means of extension coil springs 9e. The fitting tubes 9d and 9d act to hold the cellular phone 2 from the opposite sides in a direction of width thereof, as a holding part.

The fitting tubes 9d and 9d are provided on its top part with holding members 9c and 9c which hold the cellular phone from its direction of thickness in cooperation with the main body. The holding members 9c and 9c are provided with an extension coil spring 9f. The fitting tubes 9d are biased to approach with respect to each other by the extension spring 9f. The cellular phone 2 is inserted in a space 10 that is surrounded by the fitting tubes 9d, the main body 6, and the holding members 9c and then set in the portable ophthalmic apparatus 1.

Figure 4:
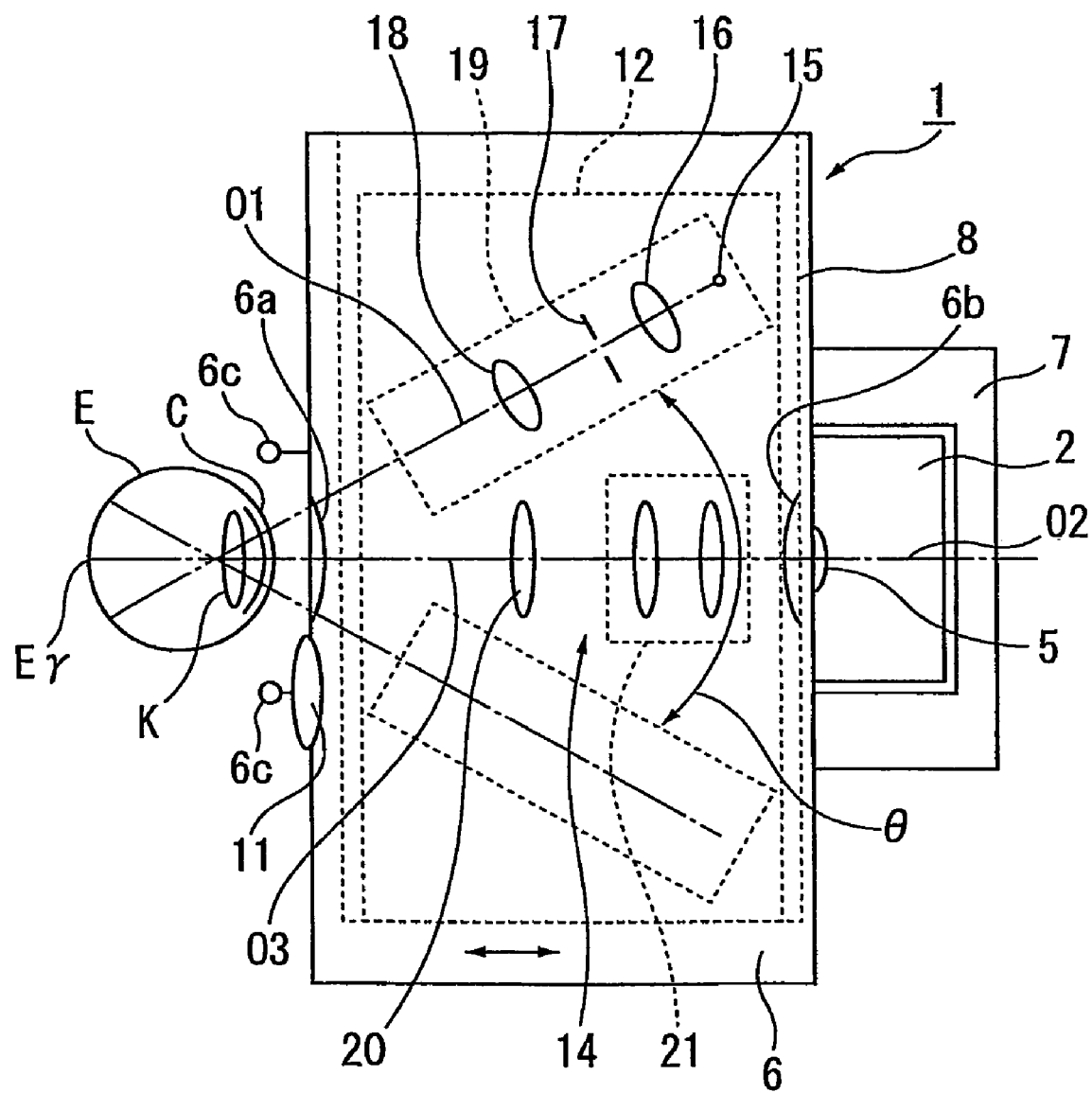
FIG. 4 is an optical view showing an example of an optical unit to be set on a main body as shown in FIG. 1, which is also an explanatory view showing a used state in conducting a photograph of cross-sectional images of a cornea and a crystalline lens.

As shown in FIG. 4, the main body 6 has at opposite central parts thereof round-shaped windows 6a and 6b. The round-shaped window 6a is placed on the side that faces photographing objective eyes E. The round shaped window 6b is located on the side that faces a photographing lens 5 of the cellular phone 2. In addition, in the FIG. 4, C shows a cornea, Er an eye ground, and K a crystal line lens.

The main body 6 is provided with a pair of light sources 6c and 6c (white color light sources) for illuminating an anterior ocular segment of the eye in the side on which the round-shaped window 6a is set and the pair of light sources are symmetrically placed across the round-shaped window 6a. An auxiliary lens 11 is set detachably on the round-shaped window 6a to observe the eye ground.

An optical unit 12 is set detachably on the main body 6. The optical unit 12 is composed of an illumination optical system 13 and a photographical assistant optical system 14. An illumination optical axis O1 of the illumination optical system 13 is designed to intersect with a photographing optical axis O2 of the photographing lens 5 at a predetermined angle.

The illumination optical system 13 is schematically composed of illumination system components such as an illumination light source 15, a condenser 16, a slit aperture stop 17, a projection lens 18 and so on. The slit aperture stop 17 is adapted to be capable of changing the slit width. These illumination system components are disposed in a lens barrel 19. As shown in FIG. 4, the lens barrel 19 is designed to be capable of rotating in order to change a predetermined angle θ relative to the photographing optical axis O2 within the range of the angle. The photographical assistant optical system 14 is schematically composed of an objective lens 20 and a zoom lens system 21.

As shown in FIG. 5, the optical unit 12 is provided with a control part 22, a first drive part 23, a second drive part 24, a third drive part 25, a fourth drive part 26, an operating part 27, and a power part 28.

As a power source of the power part 28, a battery or the like may be used. The operating part 27 has an on/off switch that turns on or off the power part 28, drive switches that drive the first to fourth drive parts 23 through 26, the illumination light source 15 and an on/off switch that turns on or off the light sources 6c and 6c for illuminating the anterior ocular segment. The cellular phone 2 has a photographing camera, a ten-key operating portion 4, a monitor portion 3, and a telecommunication facility part. The photographing camera portion is provided with a shutter button.

Based on an operation of the operating part 27, the control part 22 controls the first to fourth drive parts 23 to 26 and the power part 28. The first drive part 23 achieves the role of inserting and removing the auxiliary lens for observation of the retina 11. The second drive part 24 acts to cause the illumination optical system 13 to rotate. The third drive part 25 achieves the role of driving the zoom lens system 21. The fourth drive part 26 achieves the role of driving the entire optical unit 12 forwardly and backwardly (directions of photographing optical axis). An explanation for any mechanical structure relating to the driving is omitted.

Figure 6:
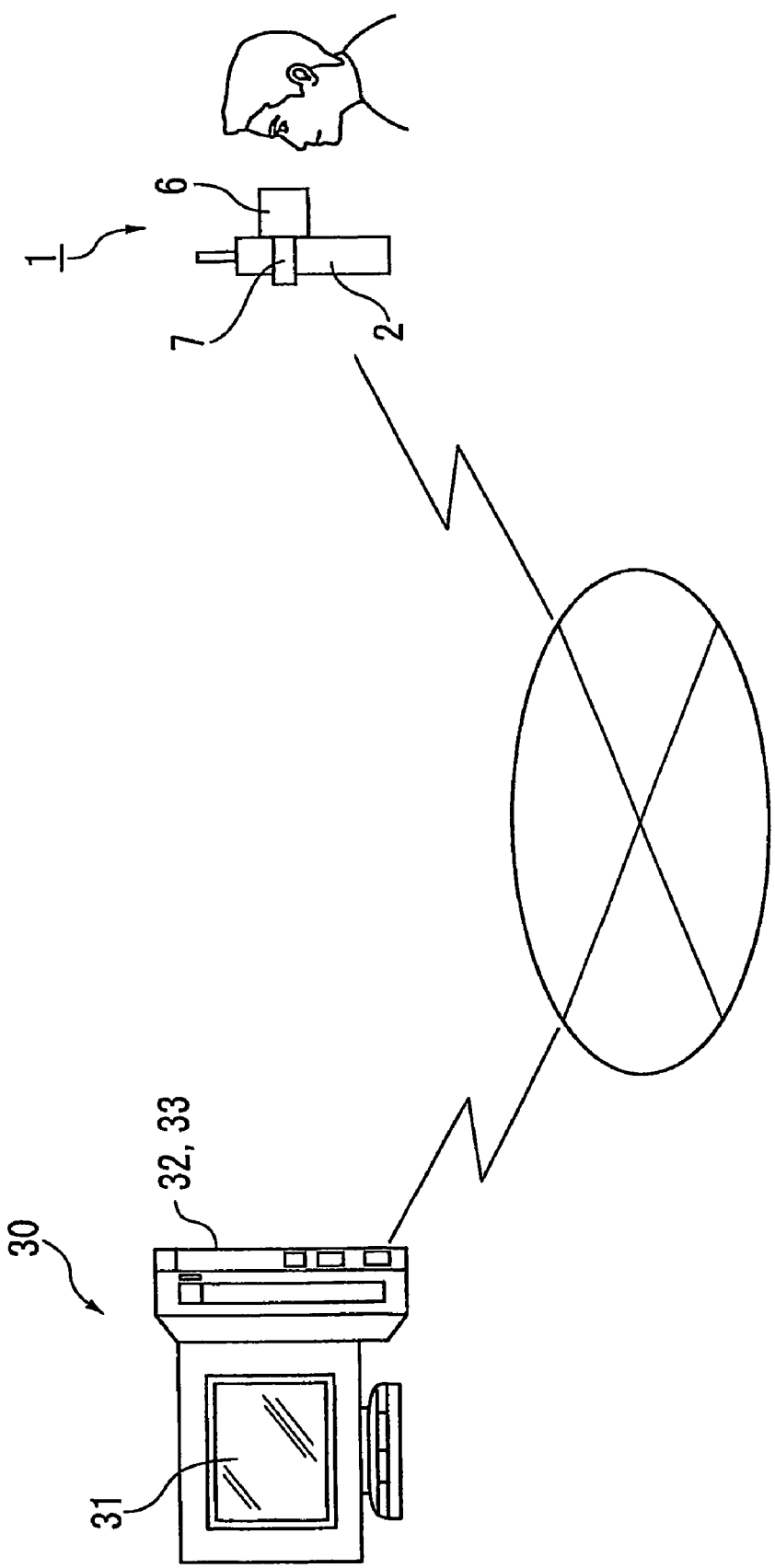
FIG. 6 is an explanatory view of a system of the portable ophthalmic apparatus according to the present invention.

As shown in FIG. 6, the portable ophthalmic apparatus 1 is connected to a server 30 through the Internet. The server 30 has a monitor (display part) 31, an arithmetic part 32, and a memory part 33. The graphic data of photographing objective eyes that are taken by the photographing camera of the cellular phone 2 are transmitted through the Internet and then processed.

Next, an example of industrial applicability of the portable ophthalmic apparatus according to the present invention will be explained.

Figure 7:
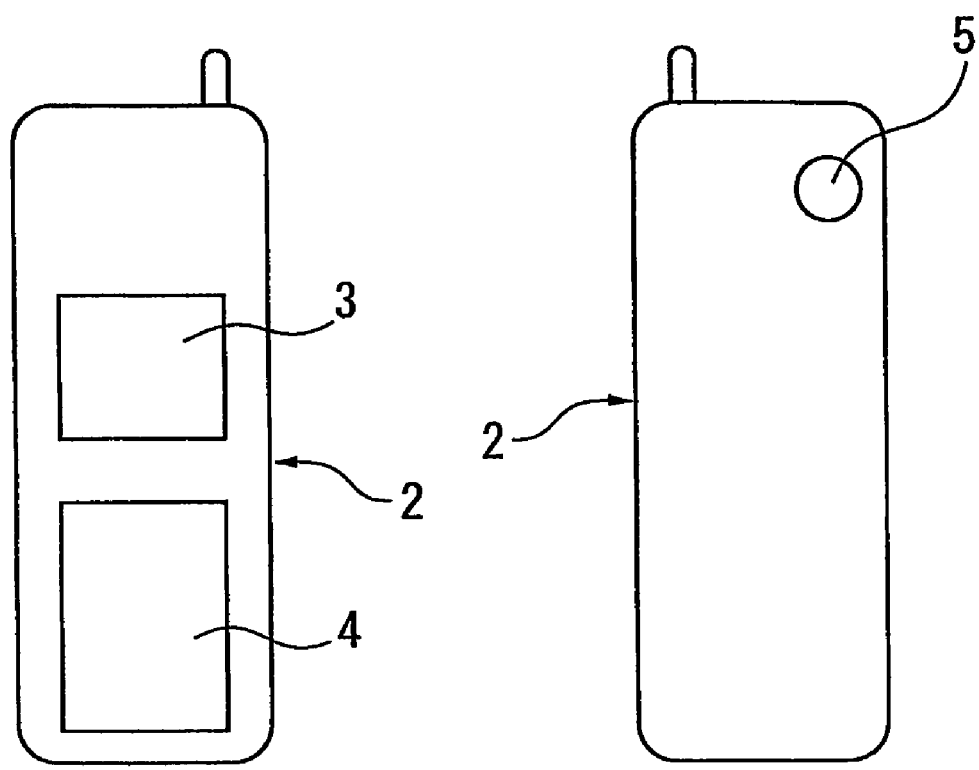
FIG. 7 is a schematic diagram showing the other structure of the cellular phone, in which (a) is a front view of the cellular phone, and (b) is a back view of the cellular phone shown in (a).

First, the supporting part 7 is adjusted based on the type of portable devices. For instance, as shown in FIGS. 7(a) and (b), if the photographing camera 5 corresponds to the cellular phone 2 which is not set in the central part in its width direction, but shifted from its one side, the cellular phone 2 is attached to the main body 6 by sliding the cellular phone 2 along the dovetail groove 8 so as to roughly coincide the optical axis O2 of the photographing camera 5 with the optical axis O3 of the photographical assistant lens system 14 as shown in FIG. 8.

If the portable device corresponds to a PDA 2', it is attached to the main body 6 by adjusting center distance of the legs 9 and 9 and height of the fitting tube 9d and 9d to extend the legs as shown in FIG. 3, and then adjusting the optical axis O2 of the photographing camera of the portable device and the optical axis O3 of the photographing assistant lens system 14 to roughly coincide them. In case of the cellular phone 2 shown in FIG. 1, it is set in the main body 6 so that the supporting part 7 is approximately positioned in the center part of the cellular phone 2.

Then, by operation of the operation part 27, functions are set up. Here, a photographing in the slit illumination is chosen. Next, the conditions for illumination and photographing are set up.

For instance, the conditions for illumination are an amount of illumination beam, an angle formed between the photographing optical axis O1 and the illumination optical axis O2, and a shape of illumination beam. The shape of the illumination beam can be changed by means of change of the shape of the slit aperture stop 17. The conditions of photographing are, for instance, an exposure time, and a photographical magnification (zoom magnification).

Then, an alignment is carried out in such a manner that the photographing objective eyes E of the subject (patient) are reflected in the center of the monitor display part 3 of the cellular phone 2. At that time, the light source 6c for illuminating anterior ocular segment is used.

Then, the optical unit 12 is moved in the direction of the optical axis to conjugate the cornea C and the photographing camera 5. Then, graphic data of the photographing objective eyes E is taken by operation of a shutter button.

Figure 10:
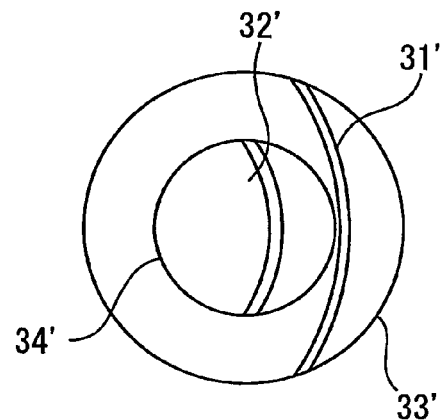
FIG. 10 is a view of cross-sectional images of a cornea and a crystalline lens photographed by the optical unit shown in FIG. 4.

Then, literal data and command are entered by operation of the ten-key part 4 into the cellular phone 2. Then, by pushing a sending button, the graphic data, the literal data representing a relationship with the subject, and command are transmitted to the server 30 through the Internet. At the server 30, processes are carried out based on those graphic data and command. The server 30 checks about whether there is a return command. FIG. 10 shows an example of a photographic image taken by the slit illumination. In FIG. 10, 31' denotes a cross-section image of cornea, 32' a cross-section image of crystalline lens, 33' a rainbow borderline, and 34' an edge of a pupil.

The server 30 transmits the result of process to the cellular phone 2 if there is a return command. The processed result is displayed on the monitor display part 3. If the photographing continues to be carried out, this process is repeated. If the process is discontinued, the power source of the operating part 27, or either the power source or transmitting of the cellular phone 2 should be turned off.

Figure 11:
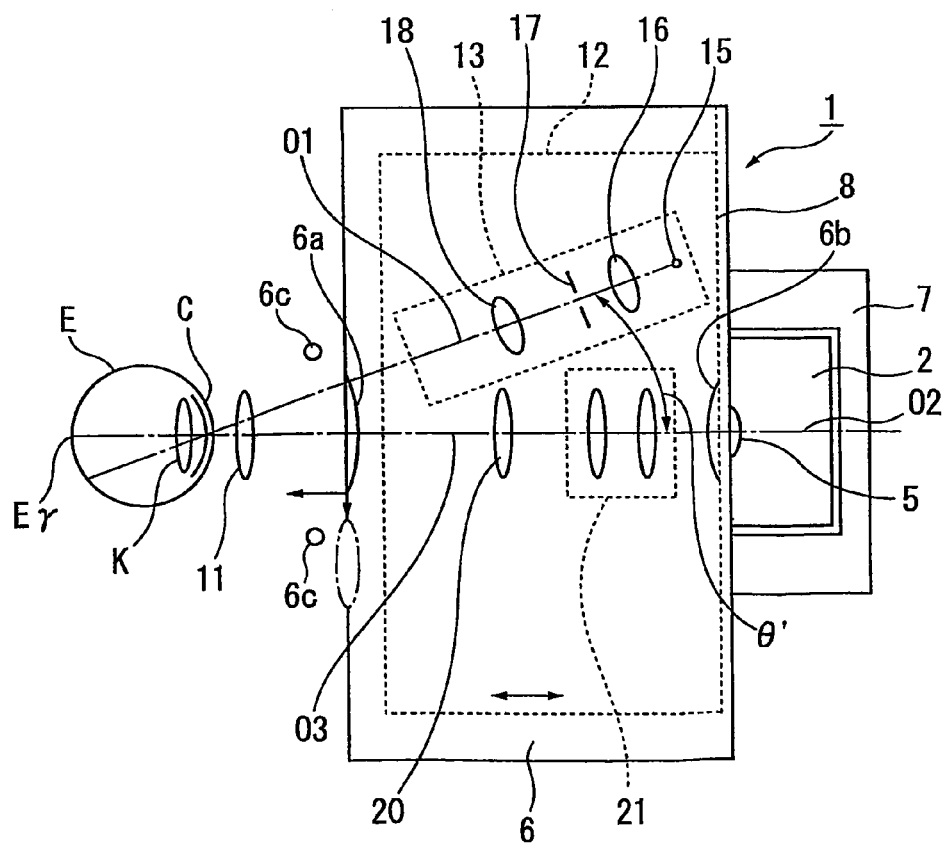
FIG. 11 is an explanatory view showing a busy condition of photographing an eye ground by utilizing the optical unit shown in FIG. 4.

In the case of observation for the eye ground, as shown in FIG. 11, an angle θ' formed between the illumination optical axis O1 of the illumination optical system and the photographing optical axis O2 is set to become smaller than the angle as in the slit illumination observation. By operating the operating part 27, the auxiliary lens 11 is placed in front of the round-shaped window 6a so that it is placed in a photographical light path. In addition to this, the auxiliary lens 11 is moved along the optical axis and set to conjugate the retina Er of the photographing objective eyes E and the photographing lens 5.

Also, in the same way, by pushing the shatter button, graphic data are taken in the cellular phone 2 and are then transmitted similarly.

Figure 12:
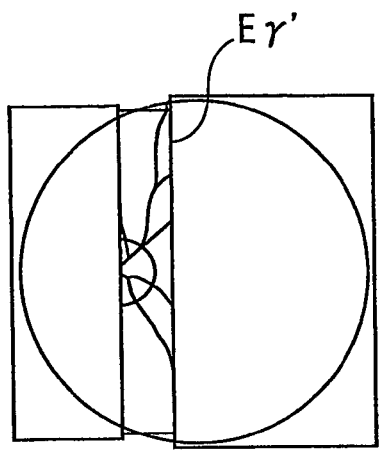
FIG. 12 is a view of a fundus photographed by utilizing the optical unit shown in FIG. 4.

FIG. 12 shows an example of an image Er' of the eye ground taken in such manners.

Also, it is possible to preserve these eye ground image Er', cross-section image of cornea 31', and cross-section image of crystalline lens 34' as electronic cartels.

(Mode 2 for Carrying Out the Invention)

Figure 13:
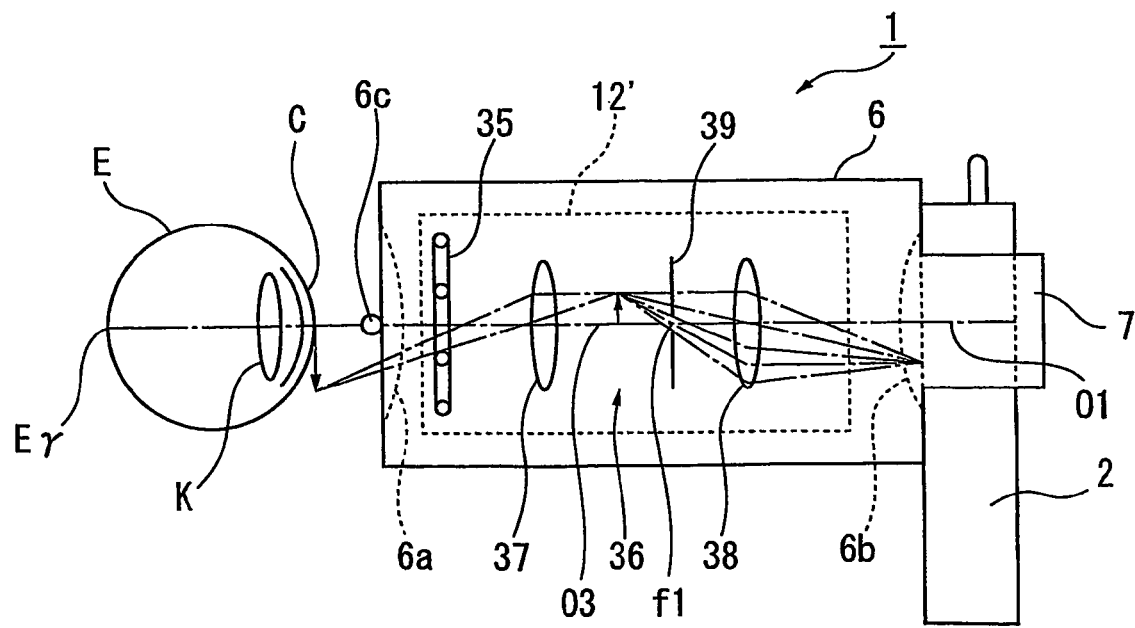
FIG. 13 is a view of the portable ophthalmic apparatus in which the optical unit containing an illumination optical system of a placido-disc is set to the main body.

FIG. 13 shows a state that as the optical unit 12, an optical unit 12' which has a placido-disc illumination optical system is set in the main body 6. Here, the optical unit 12' has a concentric placido-disc illumination light source 35 and a photographical assistant lens optical system 36. The photographical assistant lens optical system 36 has a pair of relay lenses 37 and 38. A telecentric aperture stop 39 is set in a front focus point f1 of the relay lens 38.

With this apparatus, a concentric placido-disc illumination light is projected to each cornea C of the photographing objective eyes (examined eyes) E. A placido-disc image formed on the surface of the cornea C is once focused in air by means of the relay lens 37, The image focused in air passes through the telecentric aperture stop 39, then through the relay lens 38 it is lead to the photographing camera 5 and is focused again thereon. By doing this, the graphic data of the placido-disc image are entered in the cellular phone 2.

Figure 14:
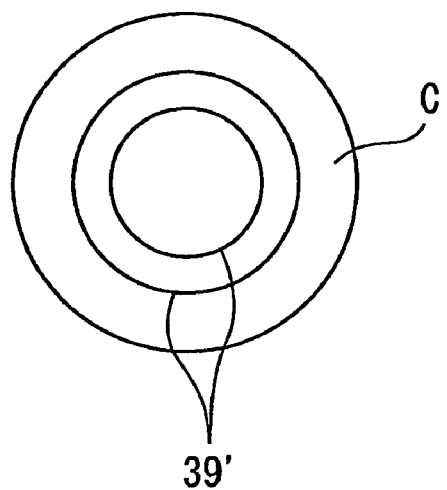
FIG. 14 is an explanatory view of a placido disc image photographed by utilizing the optical unit shown in FIG. 13.

FIG. 14 shows a placido-disc image 39' formed on the surface of the cornea. In the mode, the number of rings is two, but, the number may be increased without limited. The server 30 analyzes a shape and an interval of the placido-disc image 39' to obtain the shape of the cornea in accordance with contents of command. The analyzed processing result is transmitted to the cellular phone 2 by the command.

(Mode 3 for Carrying Out the Invention)

Figure 15:
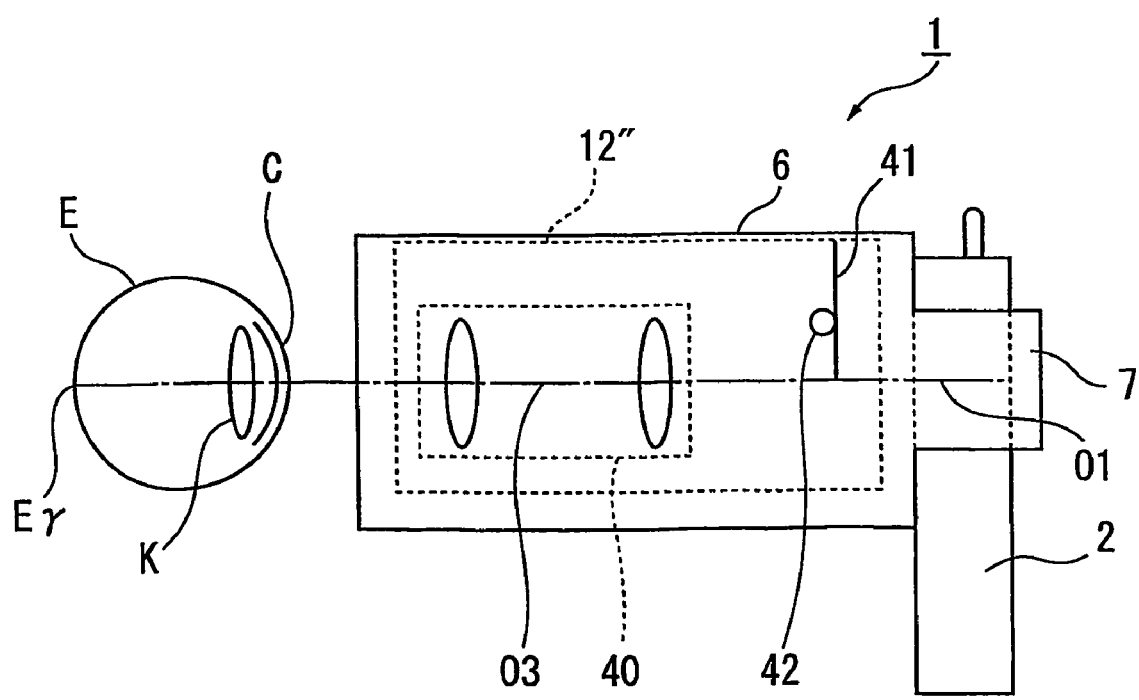
FIG. 15 is a view showing an example of the portable ophthalmic apparatus in which an optical unit for measuring refractivity by retinoscopy is set in the main body.

In a mode 3, as the optical unit 12, an optical unit 12" which measures reflecting power of an eye with retinoscopy is set in the main body as shown in FIG. 15. The optical unit 12" is composed of a telescope part 40 as the photographing assistant lens system, a knife-edge 41, and an illumination light source 42.

Here, the illumination light source 42 is disposed in a position where is out of the photographing optical axis O1 and conjugated with the knife-edge 41 to radiate infrared ray toward the retina Er.

Figure 16A:
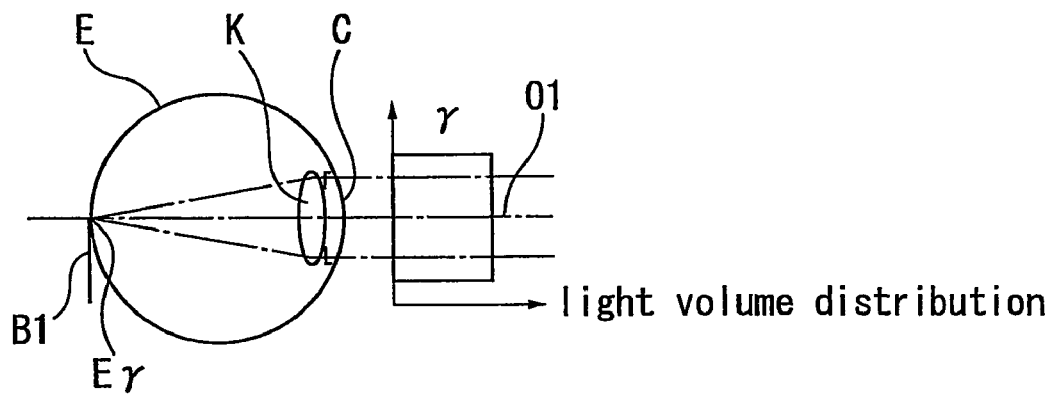
FIG. 16 is an explanatory view for explaining a principle of the retinoscopy, in which (a) is a view of a subject eye in case of normal vision, and (b) is a view of a subject eye in case of myopia, and (c) is a view of a subject eye in case of hyperopic.
Figure 16B:
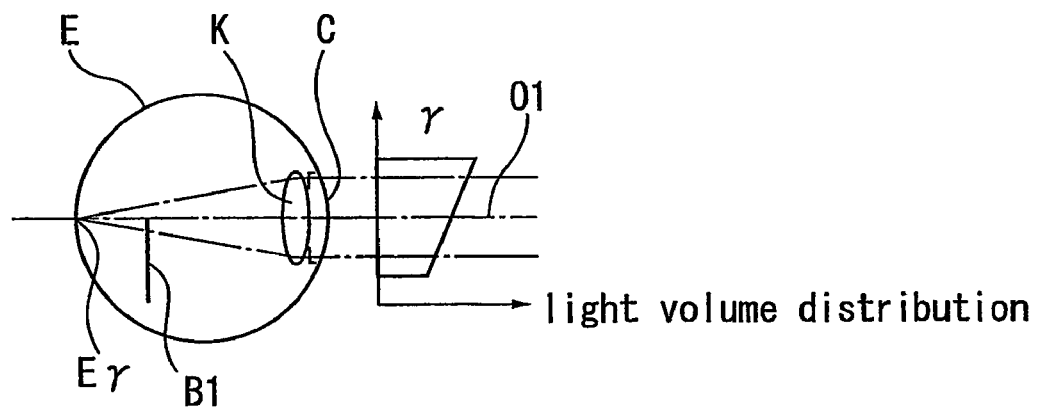
Figure 16C:
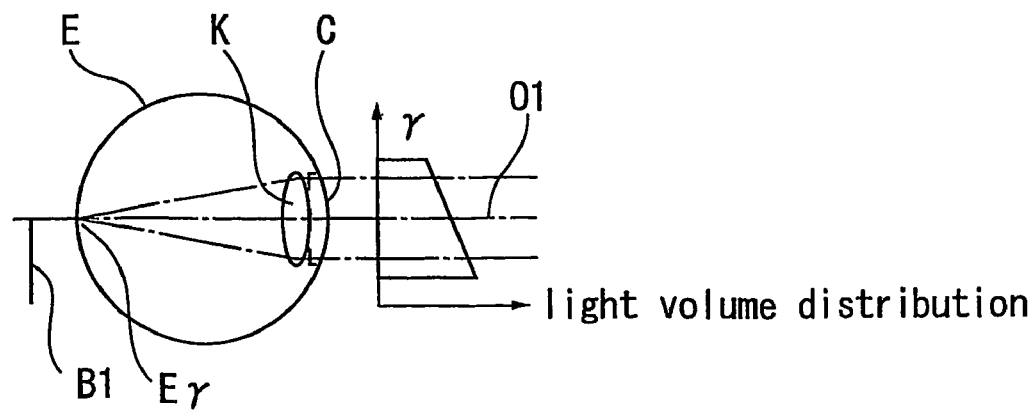

If the subject eye E is normal vision, as shown in FIG. 16(a), an image B1 is formed on the cornea of the eye ground Er. If myopia, as shown in FIG. 16(b), an image B1 is formed in front of the cornea of the eye ground Er. If longsighted eye, as shown in FIG. 16(c), an image B1 is formed back of the cornea of the retina Er.

With the retinoscopy, reflectivity is obtained from light volume distribution. Namely, reflectivity is obtained from the light volume distribution from the eye ground Er that is appeared in a papillary zone of the subject eye E. Also, either the myopia or hyperopia is determined by observing whether bright part of the reflected light coming from the eye ground Er is on the same side or the opposite side of the knife edge 41.

In normal vision, light volume distribution in r-direction perpendicular to the optical axis O1 is equivalent. In myopia, reflected light volume increases toward the same side as the knife edge 41. In hyperopia, reflected light volume decreases toward the same side as the knife edge 41 and increases toward the opposite side. Also, as spherical degree of the eye increases, a difference of the light volume distribution becomes large. By photographing the reflected light volume with the photographing camera 5, reflectivity is obtained.

Then, by enlarging the pupil with the telescope part 40, taking in the image of the pupil as a graphic data in the cellular phone 2 with the photographing camera 5, transmitting the graphic data to the server 30, analyzing and processing it at the server 30 side, reflectivity (spherical degree) of the objective eye E is finally obtained.

Figure 17:
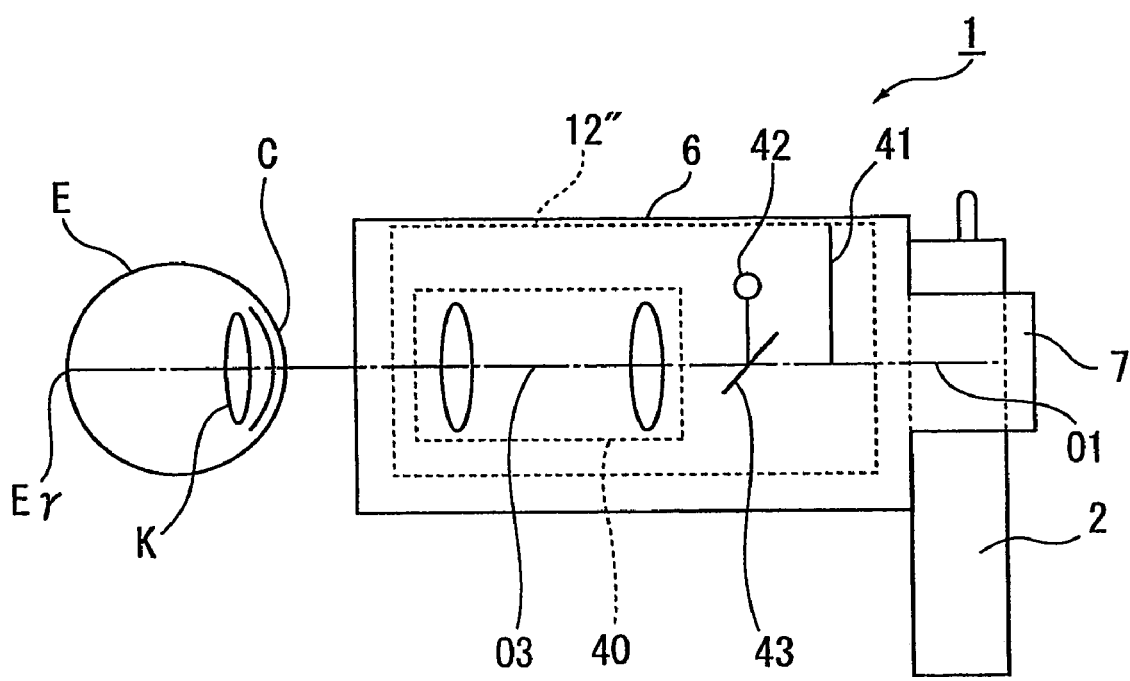
FIG. 17 is a view showing another example of the portable ophthalmic apparatus in which the optical unit for measuring refractivity with retinoscopy is set to the main body.

In this case, the photographing is carried out with setting the illumination light source 42 off the photographing optical axis. However, the illumination light source 42 may be set on the photographing optical axis O1 and also may be set in a position conjugated with the knife-edge 41. FIG. 17 shows an example thereof and numeral 43 is a half miller. The light source 42 is set in the conjugated position though the knife-edge 41 and the half miller 43. The image of the light source 42 is formed on the optical axis O1 which is in the edge end of the knife-edge 41.

As described above, although the modes for carrying out the present invention are explained, if the portable device is a digital camera that has a zoom lens and a macroscopic, the photographing assistant optical system 14 and 36 need not be set.

Also, a predetermined analyzing software is installed in the portable device to analyze facts having no complex process such as optical reflecting power without transmitting data to the server. Furthermore, if the portable device is such as a digital camera that has no a wireless communication mean, the data may be temporally stored in the portable device and thereafter the date may be transferred by connection with the server.

Further, by providing a blue colored filter in the illumination optical system 12 and then illuminating the anterior ocular segment of subject by the blue colored illumination beam as well as using a fluorescein, observational photographing of the fluorescence portion (so called, observation of fluorescein staining findings) can be carried out.

INDUSTRIAL APPLICABILITY

The present invention is designed in accordance with the above so that the graphic data of photographing objective eyes can be easily obtained with the prevailing portable devices having the photographing function such as the cellular phone, personal digital assistance (PDA), and digital camera and so on.

The invention claimed is:

1. A portable ophthalmic apparatus comprising:
a supporting part which attaches detachably to a portable device having a photographing camera part on a photographing optical axis; and
a main body which is arranged integrally with said supporting part and which comprises an illumination optical system for radiating an illumination beam toward photographing objective eyes along an illumination optical axis intersected at a predetermined angle with said photographing optical axis,
wherein said illumination optical system comprises a slit opening stop and wherein, by projecting a slit illumination beam toward said photographing objective eyes, sectional shapes of a cornea and a crystal lens are photographed.

2. A portable ophthalmic apparatus comprising:
a supporting part which attaches detachably to a portable device having a photographing camera part on a photographing optical axis; and
a main body which is arranged integrally with said supporting part and which comprises an illumination optical system for radiating an illumination beam toward photographing objective eyes along an illumination optical axis intersected at a predetermined angle with said photographing optical axis,
wherein said main body comprises a concentric placido-disc illumination optical system and wherein a cornea of each of said photographing objective eyes is ring-illuminated.

3. A portable ophthalmic apparatus comprising:
a supporting part which attaches detachably to a portable device having a photographing camera part on a photographing optical axis; and
a main body which is arranged integrally with said supporting part and which comprises an illumination optical system for radiating an illumination beam toward photographing objective eyes along an illumination optical axis intersected at a predetermined angle with said photographing optical axis,
wherein said supporting part comprises a pair of legs which are movable to approach and move away or extend and contract with respect to each other.

4. A portable ophthalmic apparatus comprising:
a supporting part which attaches detachably to a portable device having a photographing camera part on a photographing optical axis; and
a main body which is arranged integrally with said supporting part and which comprises an illumination optical system for radiating an illumination beam toward photographing objective eyes along an illumination optical axis intersected at a predetermined angle with said photographing optical axis,
wherein an illumination condition of said illumination optical system is changeable, and
wherein said illumination optical system comprises a slit opening stop and wherein, by projecting a slit illumination beam toward said photographing objective eyes, sectional shapes of a cornea and a crystal lens are photographed.

5. A portable ophthalmic apparatus comprising:
a supporting part which attaches detachably to a portable device having a photographing camera part on a photographing optical axis; and
a main body which is arranged integrally with said supporting part and which comprises an illumination optical system for radiating an illumination beam toward photographing objective eyes along an illumination optical axis intersected at a predetermined angle with said photographing optical axis,
wherein an illumination condition of said illumination optical system is changeable, and
wherein said main body comprises a concentric placido-disc illumination optical system and wherein a cornea of each of said photographing objective eyes is ring-illuminated.

6. A portable ophthalmic apparatus comprising:
a supporting part;
a main body which is integrally with said supporting part and which attaches detachably to a portable device via said supporting part, said portable device having a photographing camera part;

an illumination optical system which is in said main body and which radiates an illumination beam toward at least one photographing objective eye along an illumination optical axis intersected at a predetermined angle with a photographing optical axis of said portable device; and an objective lens disposed in said main body such that an optical axis of said objective lens substantially coincides with said photographing optical axis.

7. A portable ophthalmic apparatus according to claim 6, wherein an illumination condition of said illumination optical system is changeable, and wherein the illumination condition depends upon an angle formed between said photographing optical axis and said illumination optical axis, or a shape or a volume of said illumination beam.

8. A portable ophthalmic apparatus according to claim 7, wherein said main body comprises a photographing assistant optical system which is configured in such a manner that a photographic condition of the photographing assistant optical system is changeable in accordance with changing of said illumination condition.

9. A portable ophthalmic apparatus according to claim 8, wherein said photographing assistant optical system comprises a zoom lens and an auxiliary lens, and wherein the auxiliary lens is set and position of zoom of the zoom lens is changeable in accordance with the photographic condition.

10. A portable ophthalmic apparatus according to claim 6, wherein said illumination optical system comprises a slit opening stop and wherein, by projecting a slit illumination beam toward the photographing objective eyes, sectional shapes of a cornea and a crystal lens are photographed.

11. A portable ophthalmic apparatus according to claim 6, wherein said main body comprises a concentric placido-disc illumination optical system and wherein a cornea of each of the photographing objective eyes is ring-illuminated.

12. A portable ophthalmic apparatus according to claim 6, wherein said supporting part comprises a pair of legs which are movable to approach and move away or extend and contract with respect to each other.

13. A portable ophthalmic apparatus according to claim 6, wherein said supporting part is slidable relative to said main body.

14. A portable ophthalmic apparatus according to claim 6, wherein said portable device is a personal digital assistant having a telecommunication function part.

15. A portable ophthalmic apparatus according to claim 6, wherein said main body comprises a photographing assistant optical system for photographing an eye ground of the photographing objective eyes, and wherein said illumination optical system is adapted to change an angle which is formed between said photographing optical axis and illumination optical system.

16. An ophthalmic system according to claim 15, wherein said portable device is configured to transmit at least one of literal data and symbol data together with said graphic data.

17. An ophthalmic system comprising a portable ophthalmic apparatus that comprises:

a supporting part;

a main body which is arranged integrally with said supporting part and which attaches detachably to a portable device via said supporting part, said portable device having a photographing camera part;

an illumination optical system which is provided in said main body and which radiates an illumination beam toward at least one photographing objective eye along an illumination optical axis intersected at a predetermined angle with a photographing optical axis of said portable device; and an objective lens disposed in said main body such that an optical axis of said objective lens substantially coincide with said photographing optical axis, wherein the portable device has a telecommunication function part and a command function to process graphic data of the photographing objective eyes at an end destination.

\* \* \* \* \*